United States Patent [19]

Blackwell et al.

[11] Patent Number: 5,645,429
[45] Date of Patent: Jul. 8, 1997

[54] METHOD FOR ADHERING TO TOOTH STRUCTURE

[75] Inventors: Gordon Blackwell, Konstanz, Germany; Chin-Teh Huang, Dover; Steven Jefferies, Milford, both of Del.

[73] Assignee: Dentsply Research & Development Corp., Milford, Del.

[21] Appl. No.: 642,808

[22] Filed: May 3, 1996

Related U.S. Application Data

[63] Continuation of Ser. No. 294,931, Aug. 26, 1994, abandoned, which is a continuation-in-part of Ser. No. 292,104, Aug. 22, 1994, abandoned.

[51] Int. Cl.$^6$ .................................................. A61K 6/08
[52] U.S. Cl. ....................... 433/217.1; 523/118; 523/115; 524/559; 524/547; 524/361
[58] Field of Search ................. 433/217.1; 523/115, 523/118; 524/559, 361, 547

[56] References Cited

U.S. PATENT DOCUMENTS

| | | | |
|---|---|---|---|
| 3,785,832 | 1/1974 | Bowen | 433/217.1 |
| 3,884,886 | 5/1975 | Pluddemann | 526/279 |
| 4,107,845 | 8/1978 | Lee, Jr. et al. | 523/116 |
| 4,182,035 | 1/1980 | Yamauchi et al. | 523/118 |
| 4,499,251 | 2/1985 | Omura et al. | 433/228.1 |
| 4,514,342 | 4/1985 | Billington et al. | 526/277 |
| 4,515,930 | 5/1985 | Omura et al. | 524/547 |
| 4,525,256 | 6/1985 | Martin | 522/14 |
| 4,537,940 | 8/1985 | Omura et al. | 524/547 |
| 4,540,722 | 9/1985 | Bunker | 523/109 |
| 4,544,467 | 10/1985 | Bunker et al. | 433/217.1 |
| 4,553,941 | 11/1985 | Aasen | 433/228.1 |
| 4,593,054 | 6/1986 | Asmussen et al. | 523/118 |
| 4,636,533 | 1/1987 | Janda et al. | 522/14 |
| 4,640,936 | 2/1987 | Janda et al. | 522/14 |
| 4,645,456 | 2/1987 | James | 433/217.1 |
| 4,669,983 | 6/1987 | Bunker | 433/217.1 |
| 4,670,576 | 6/1987 | Bunker | 523/115 |
| 4,719,149 | 1/1988 | Aasen et al. | 523/116 |
| 4,816,495 | 3/1989 | Blackwell et al. | 523/116 |
| 4,855,475 | 8/1989 | Bunker | 558/182 |
| 4,863,993 | 9/1989 | Montgomery | 524/317 |
| 4,872,936 | 10/1989 | Engelbrecht | 523/118 |
| 4,880,660 | 11/1989 | Aasen et al. | 427/2 |
| 4,913,939 | 4/1990 | Montgomery | 427/389 |
| 4,929,746 | 5/1990 | Bunker | 558/92 |
| 4,945,006 | 7/1990 | Muggee et al. | 526/305 |
| 4,948,366 | 8/1990 | Horn et al. | 433/9 |
| 4,948,367 | 8/1990 | Haas | 433/9 |
| 4,966,934 | 10/1990 | Huang et al. | 523/118 |
| 5,064,495 | 11/1991 | Omura et al. | 526/288 |
| 5,085,726 | 2/1992 | Omura et al. | 433/217.1 |
| 5,089,051 | 2/1992 | Eppinger et al. | 523/118 |
| 5,091,441 | 2/1992 | Omura | 523/176 |
| 5,141,436 | 8/1992 | Orlowski | 433/9 |
| 5,177,121 | 1/1993 | Bunker | 524/547 |
| 5,186,783 | 2/1993 | Kawashima et al. | 156/307.3 |
| 5,218,070 | 6/1993 | Blackwell | 523/113 |
| 5,252,629 | 10/1993 | Imai et al. | 523/118 |
| 5,254,198 | 10/1993 | Kawashima et al. | 526/286 |
| 5,256,447 | 10/1993 | Oxman et al. | 526/278 |
| 5,264,513 | 11/1993 | Ikemura et al. | 523/118 |
| 5,295,824 | 3/1994 | Wong | 433/9 |
| 5,295,825 | 3/1994 | Betush | 433/28 |
| 5,304,585 | 4/1994 | Bunker | 523/118 |

FOREIGN PATENT DOCUMENTS

| | | | |
|---|---|---|---|
| 2201475 | 7/1973 | Germany | 433/217.1 |
| 8502112 | 5/1985 | WIPO | 433/217.1 |

OTHER PUBLICATIONS

Caulk, Technique Manual, Step–by–Step Procedures for the Cosmetic Repair of Dental Defects, Second Edition (1990).
Caulk, Prisma APH, VLC Hybrid Composite (1990).
Gunnar Ryge, vol. 30, No. 4, Clinical Criteria, pp. 347–358 (1988).
John F. Cvar and Gunnar Ryge, Clinical Evaluatition of Dental Restorative Materials, U.S. Department of Health Education and Welfare, pp. 1, 10 and 11 Appendix II (1985).

*Primary Examiner*—Andrew E. C. Merriam
*Attorney, Agent, or Firm*—Dale R. Lovercheck; James B. Bieber

[57] ABSTRACT

A method is provided for clinical retention of restorative material by a natural tooth. A first portion of photopolymerizable liquid primer/adhesive dental composition is applied to a tooth surface. After leaving the first portion of the liquid composition on the tooth surface undisturbed for at least 15 seconds on the tooth surface air is conveyed against the first portion of the liquid. The light is impinged on the first portion of the liquid composition whereby at least a portion of the first portion of the liquid composition polymerizes to form a first coating on the tooth. A second portion of the liquid composition is applied to the first coating, and air is substantially immediately conveyed to the second portion of the liquid composition. Light is then impinged on the first and second portions of the liquid composition whereby at least a portion of the second portion of the composition polymerizes to form a treated tooth surface adapted to retain a restorative material at a clinical retention rate of at least 98 percent with acceptable marginal integrity.

43 Claims, No Drawings

METHOD FOR ADHERING TO TOOTH STRUCTURE

This is a continuation of application Ser. No. 08/294,931, filed Aug. 26, 1994 now abandoned, which is a continuation-in-part of application Ser. No. 08/292,104, filed Aug. 22, 1994, now abandoned.

The invention relates to a method of adhesion of restoratives to teeth. The invention provides a method for adhering restorative to dental tooth surface with a high rate of clinical retention, high bond strength and acceptable marginal integrity. At least two portions of the composition are applied. Each portion is cured separately after each is applied or both portions are cured initially after both portions are applied. Restorative material is then applied to the treated tooth surface and cured to form a bond with a bond strength of at least about 12 MPa, acceptable marginal integrity and a high rate of clinical retention. The method of the invention provides acceptable marginal integrity, substantially improves bond strength of dental restoratives to natural teeth and increases the percent of restorative retention to natural teeth to at least 95 percent without etching, and to at least 98 percent with etching. This restorative retention is provided without any mechanical retention, for example by under cutting tooth material.

It is most desirable, when filling a tooth cavity with a filling material, such as a polymerizable dental restorative, to ensure good adhesion between the tooth surrounding the cavity and the set (polymerized) filling material. A good seal between the set filling material and the tooth prevents, or at least markedly inhibits, ingress of mouth fluids and bacteria into the filled cavity and thus prevents further decay or loss of the filling material. In order to achieve good adhesion between the filler material and the tooth enamel, it has been recommended to separately apply from separate container provide a primer and an adhesive. The primer and the adhesive form a bonding layer intermediate the filling material and surfaces of a prepared tooth. The prior art does not disclose a method of adhering polymerizable acrylate containing restoratives to dentin by twice applying a priming adhesive composition from the same container to provide improved retention, acceptable marginal integrity and a bond strength of at least 12 MPa as is provided by the present invention.

Bowen in U.S. Pat. No. 3,785,832 discloses Dental Primer varnish. Pluddemann in U.S. Patent No. 3,884,886 discloses Cationic Unsaturated Amine-Functional Silane Coupling Agents. Lee, Jr. et al in U.S. Pat. No. 4,107,845 discloses Dental Adhesive Composites. Yamauchi et al in U.S. Pat. No. 4,182,035 discloses Adhesive Compositions for the Hard Tissues of the Human Body. Omura et al. in U.S. Pat. No. 4,499,251 discloses Adhesive Compositions. Billington in U.S. Pat. No. 4,514,342 discloses Polyethylenically Unsaturated Monophosphates. Omura et al in U.S. Pat. No. 4,515,930 discloses Highly Water-Resistant Adhesive. Martin in U.S. Pat. No. 4,525,256 discloses Photopolymerizable Composition Including Catalyst Comprising Diketone Plus. Omura et al. in U.S. Pat. No. 4,537,940 discloses Adhesive Compositions. Bunker in U.S. Pat. No. 4,540,722 discloses Dentin and Enamel Adhesive. Bunker in U.S. Pat. No. 4,544,467 discloses Light-Curable Dentin ad Enamel Adhesive. Aasen in U.S. Pat. No. 4,553,941 discloses Acetal and Hemiacetal Dentin and Enamel Adhesive Primers. U.S. Pat. No. 4,589,756 relates to similar aromatic based compositions employed in dentistry. Asmussen et al. in U.S. Pat. No. 4,593,054 disclose Adhesion Promoting Agent, Process for its preparation and use thereof on Collageneous Material. Janda in U.S. Janda in U.S. Pat. No. 4,636,533 discloses Photopolymerizable Adhesion Promoting Dental Composition.

Janda in U.S. Pat. No. 4,640,936 discloses Photopolymerizable Phosphate-Containing Adhesive Promoting Dental Composition. James in U.S. Pat. No. 4,645,456 discloses Adhesive Composition for Tooth Enamel. Bunker in U.S. Pat. No. 4,669,983 discloses Dentin and Enamel Adhesive. Bunker in U.S. Pat. No. 4,670,576 discloses Polymerizable Phosphorus Esters. Aasen in U.S. Pat. No. 4,719,149 discloses Method for Priming Hard Tissue. Blackwell et al in U.S. Pat. No. 4,816,495 discloses Biologically Compatible Adhesive Visible Light Curable Compositions. Bunker in U.S. Pat. No. 4,855,475 discloses (Meth)Acrylic Esters of Phosphoric Acid Ester Dihalides. Montgomery in U.S. Pat. No. 4,863,993 discloses Surface Priming Composition for Proteinaceous Substrates; Method of Making and Using Same. Engelbrecht in U.S. Pat. No. 4,872,936 teaches dental cement mixtures containing polymerizable unsaturated monomers and/or oligomers and/or prepolymers containing acid groups and/or their reactive acid-derivative groups. Aasen et al in U.S. Pat. No. 4,880,660 discloses Method for Priming Hard Tissue. Montgomery in U.S. Pat. No. 4,913,939 discloses Method of Making and Using Surface Priming Composition for Proteinaceous Substrates. Bunker in U.S. Pat. No. 4,929,746 discloses Dentin and Enamel Adhesive. Muggee et al in U.S. Pat. No. 4,945,006 discloses Low Odor Adhesive Compositions and Bonding Method Employing Same. Horn et al in U.S. Pat. No. 4,948,366 discloses Adhesive Bond Strength Control for Orthodontic Brackets. Haas in U.S. Pat. No. 4,948,367 discloses Orthodontic Accessories and Method of Applying the Same. Huang et al in U.S. Pat. No. 4,966,934 discloses Biological Compatible Adhesive Containing a Phosphorous Adhesion Promoter and Accelerator. Omura et al in U.S. Pat. No. 5,064,495 discloses Method of Adhesion with a Mercapto Group Containing Adhesive. Omura et al in U.S. Pat. No. 5,085,726 discloses Method of Adhesion with a Sulfide Group Containing Adhesive. Eppinger et al in U.S. Pat. No. 5,089,051 discloses Adhesion-Promoting Dental Composition.

Omura in U.S. Pat. No. 5,091,441 discloses Dental Composition. Orlowski in U.S. Pat. No. 5,141,436 discloses Method of Bonding Article to Teeth Employing a Light Curable Primer. Bunker in U.S. Pat. No. 5,177,121 discloses Dentin and Enamel Adhesive. Kawashima et al. in U.S. Pat. No. 5,186,783 discloses Method of Bonding with Adhesive Composition Containing a Thiocarboxylic Acid Compound. Blackwell in U.S. Pat. No. 5,218,070 discloses Dental/Medical Composition and Use. Imai et al. in U.S. Pat. No. 5,252,629 discloses Adhesives for Dentin. Kawashima et al. in U.S. Pat. No. 5,254,198 discloses Method of Bonding a Metal or Alloy Utilizing a Polymerizable Thiocarboxylic Acid or a Derivative Thereof. Oxman et al. in U.S. Pat. No. 5,256,447 discloses Adhesive Composition and Method. Ikemura et al. in U.S. Pat. No. 5,264,513 discloses Primer Composition. Wong in U.S. Pat. No. 5,295,824 discloses Plastic Bracket with Adhesive Primer Layer and Methods of Making. Betush in U.S. Pat. No. 5,295,825 discloses Control System for Dental Handpieces.

Bunker in U.S. Pat. No. 5,304,585 discloses Dentin and Enamel Adhesive. Technique Manual, Step-by-Step Procedures for the Cosmetic Repair of Dental Defects Second Edition. Prisma APH.

Dental primers and adhesives in accordance with the invention have unexpectedly superior adhesion to dentin, enamel, cavity liner, bonding materials and filling materials.

It is an object of the invention to an increase in restorative retention to a dental tooth by at least 35 percent by twice applying to the tooth a liquid composition.

It is an object of the invention to provide a method of adhering material to a tooth surface by sequentially applying portions of a liquid priming/adhesive composition to a cleaned tooth surface and curing them to form a treated tooth surface.

"Clinical retention of restorative material" as used herein refers to adhesive retention by bonding a restorative material to a natural living tooth in a patient's mouth effectively without a undercutting the tooth.

"Acceptable marginal integrity" as used herein means marginal integrity which is at least 95 percent acceptable according to the Ryge criteria after one year as being alpha or bravo in accordance with Clinical Criteria by Gunnar Ryge, Inter. Dent. J, 1980; 30(4) pages 347–358 particularly at pages 348 and 349; and Cvar er al Criteria for the Clinical Evaluation of Dental Restorative Materials, U.S. Department of Health, Education and Welfare, U.S. Public Health Service Pub. No. 790–244, U.S. Government Printing Office, 1971. Microleakage at the margin is effectively eliminated by applying restoratives with acceptable marginal integrity. "Volatile organic solvent(s) as used herein means organic solvent(s) which are substantially more volatile than water at 23° C.

"Acrylate" as used herein refers to unsaturated polymerizable compounds within the general formula:

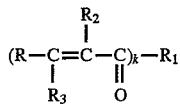

Wherein, k is an integer from 1 to 8,

R is hydrogen or methyl, $R_1$ is an alkyl having from 1 to 20 carbon atoms, $R_2$ is an alkyl having from 1 to 8 carbon atoms, and $R_3$ is an alkyl having from 1 to 12 carbon atoms.

"Water miscible volatile solvent(s)" as used herein refers to solvent(s) which are miscible with water, and when mixed with water effectively increase the vapor pressure of the water bring about to a substantial degree of increase in vaporization of water.

"Polymerizable compound" as used herein refers to monomers and/or oligomers. Acrylates are preferred polymerizable compounds.

"Phosphates" as used herein does not include pyrophosphates.

Viscosity as referred to herein is determined by a Brookfield Model LVT viscosity measuring apparatus using a number 2 spindle at 12 RPM at 25° C. A preferred viscosity a liquid priming/adhesive compositions in accordance with the invention is less than 400 centipoise (cpi), more preferably less than 300 cpi and most preferably less than 200 cpi.

SUMMARY OF THE INVENTION

A method is provided for clinical retention of restorative material by a natural tooth with acceptable marginal integrity. A first portion of photopolymerizable liquid primer/adhesive dental composition is applied to a tooth surface. After leaving the first portion of the liquid composition on the tooth surface undisturbed for at least 15 seconds on the tooth surface air is conveyed against the first portion of the liquid. The light is impinged on the first portion of the liquid composition whereby at least a portion of the first portion of the liquid composition polymerizes to form a first coating on the tooth. A second portion of the liquid composition is applied to the first coating, and air is substantially immediately conveyed to the second portion of the liquid composition. Light is then impinged on the first and second portions of the liquid composition whereby at least a portion of the second portion of the composition polymerizes to form a treated tooth surface adapted to retain a restorative material at a clinical retention rate of at least 98 percent with acceptable marginal integrity.

DETAILED DESCRIPTION OF THE INVENTION

A method of conditioning a tooth surface including applying a first portion of a liquid priming adhesive composition to a cleaned tooth surface and curing the first portion of liquid primer adhesive composition to form a primed tooth surface. Then a second portion of the liquid priming adhesive composition is applied to the primed tooth surface and cured to form a conditioned tooth surface. A polymerizable restorative composition is bonded to the tooth with a bond strength of at least about 12 MPa. Priming adhesive compositions useful in accordance with the invention preferably include in order of increasing preference at least 50, 60, 70 or 80 percent by weight of a volatile solvent and at least 15 percent by weight of a polymerizable compound.

In a preferred embodiment of the invention is provide a method of treating a natural tooth by applying a first portion of photopolymerizable liquid primer/adhesive dental composition to tooth surface to form a first coating. After leaving the first portion of the liquid composition on the tooth surface undisturbed for at least 15 seconds on the surface, a second portion of the liquid composition is applied to the first coating, and air is conveyed to the second portion of the liquid composition. Then light is impinged on the first and second portions of the liquid composition so that at least a portion of the second portion of said composition polymerizes to form a treated tooth surface adapted to retain a restorative material at a clinical retention rate of at least 98 percent.

The present invention reduces microleakage by infiltration at the interface of the restorative and the tooth.

Preferably a restorative composition is applied to a tooth surface treated in accordance with the invention, and photocured to form a restorative filling having a clinical retention rate after one year of at least 98 percent. Preferably prior to applying liquid primer/adhesive to a tooth surface the surface of smear layer of the tooth is removed, for example by acid etching by applying dilute or concentrated acid(s), or at neutral pH by applying EDTA. Thus, the photopolymerizable dental restorative composition is applied to the treated tooth surface, light is then impinged on the restorative composition whereby at least a portion of the restorative composition polymerizes to form a cured restorative material adhered with a high bond strength to the treated tooth surface.

This bond strength is greater than a comparative bond strength of a bond between the restorative material and a tooth formed essentially by applying a first portion of the liquid composition to the treated tooth surface. Then impinging light on the first portion of the liquid composition. A photopolymerizable dental restorative composition is then applied to the treated tooth surface. Light is then impinged on the restorative composition whereby at least a portion of the restorative composition polymerizes to form a cured restorative material adhered with a comparative bond strength to the treated tooth surface.

In accordance with a preferred embodiment of the invention is provided a method for clinical retention of restorative material by a natural tooth by applying a first portion of photopolymerizable liquid primer/adhesive dental composition to tooth surface. After leaving the first portion of the liquid composition on the tooth surface undisturbed for at least 15 seconds on the surface, air is conveyed (forced or directed) against the first portion of the liquid on the surface. Light is then impinged on the first portion of the liquid composition whereby a portion of the first portion of the liquid composition polymerizes to form a first coating on the tooth. A second portion of the liquid composition is applied to the first coating. Substantially immediately thereafter air is conveyed to the second portion of the liquid composition. Light is then impinged (irradiated) to the first and second portions of the liquid composition whereby at least a portion of the second portion of the composition polymerizes to form a treated tooth surface adapted to retain a restorative material at a clinical retention rate of at least 98 percent.

Preferably the first portion of the liquid composition is left on the surface undisturbed for at least 15 seconds. Preferably the solvent is miscible with water and when mixed with water substantially lowers the effective vapor pressure of the water bringing about a substantial degree of increased vaporization of the water in-situ at the treated surface. Preferably the liquid dental composition has a viscosity of less than 400 centipoise. Preferably the liquid dental composition includes oligomer having a weight average molecular weight greater than 600.

Preferably before applying the first of the liquid composition at least a portion of the tooth is treated by steps of:

(1) applying a dilute acid to the tooth surface to form an etched tooth surface, (2) rinsing the dilute acid from the etched tooth surface to form a rinsed etched surface, and (3) partially drying the rinsed etched surface to form a wetted etched surface.

Preferably the first portion of the liquid composition remains undisturbed on the surface for at least 20 seconds, and has a viscosity of less than 300 centipoise and includes at least 70% of a water miscible volatile solvent. Preferably the liquid composition includes at least 2% of an oligomer having a weight average molecular weight greater than 650.

In accordance with a preferred embodiment of the invention is provided a method of adhering a restorative material to a natural tooth by applying a first portion of photopolymerizable liquid primer/adhesive dental composition to tooth surface. After leaving the first portion of the liquid composition on the tooth surface undisturbed for at least 15 seconds on the surface, air is conveyed against the first portion of the liquid on the surface. Light is then impinged on the first portion of the liquid composition whereby a portion of the first portion of the liquid composition polymerizes to form a first coating on the tooth. A second portion of the liquid composition is applied to the first coating, and substantially immediately conveying air to the second portion of the liquid composition. Light is impinged on to the first and second portions of the liquid composition whereby at least a portion of the second portion of the composition polymerizes to form a treated tooth surface adapted to retain a restorative material at a clinical retention rate of at least 98 percent. Preferably liquid composition remains on the surface substantial undisturbed for at least 20 seconds, has a viscosity of less than 300 centipoise, includes at least 70% of a water miscible volatile solvent, and at least 2% of an oligomer having a weight average molecular weight greater than 650.

In the wet dentin techniques dentin surface is exposed and ground flat with 600 grit paper. Dentin is rinsed with clean water prior to bonding. Primer or primer/adhesive is then applied. A cotton pellet is used to remove any excess moisture on the dentin surface leaving a small amount of residual moisture on the immediate surface of the dentin.

Total Etching refers to preparation of the tooth surfaces by applying ten percent phosphoric acid for 10 to 15 seconds, then rinsing the acid off thoroughly for 10 to 15 seconds.

Shear dentin bond strengths of dentin through the Primer/Adhesive composition of the invention to Dyract Restorative Material are in excess of 18 MPa and have at least 98 percent retention of restorative. There is an extremely high percent rate of cohesive failures of 80 percent for prior art systems.

Shear dentin bond strengths achieved with primer/adhesive of the invention with TPH restorative on wet unetched dentin is 19 MPa. The shear bond strength for TPH restorative are approximately 37% higher for primer/adhesive of the invention with ProBond of the prior art.

In accordance with a preferred embodiment of the invention is provided a method of adhering a restorative material to a dental tooth by applying a dental composition which includes at least 50 percent by weight of a volatile solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which adheres to dentin with a bond strength of at least 12 MPa.

Preferably the composition includes in order of increasing preference at least 2, 2.5, 3, 3.5, 4, 5, 6, or 7 percent by weight of the multifunctional polymerizable compounds. Preferably the solvent is dimethyl ketone or methyl ethyl ketone and the bond strength is at least 15 MPa. Preferably the composition comprises at least 75 percent by weight of the solvent. Preferably at least a portion of the multifunctional polymerizable compounds are phosphate esters.

Preferably at least a portion of the multifunctional compounds have a chemical structure within the scope of the general formula:

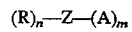

$(R)_n\text{—}Z\text{—}(A)_m$ wherein each R independently is an acrylate containing moiety, Z is an organic moiety, each A is independently is a phosphate, n is an integer greater than 2, m is an integer of 1 or more. Preferably at least a portion of the polymerizable compounds are acids and the acids comprise at least 2 percent by weight of the composition. Preferably at least a portion of the polymerizable compounds are acid esters.

In accordance with a preferred embodiment of the invention is provided a method of treating a dental tooth by applying a first portion of a liquid composition to a dental tooth surface. The polymerizable compounds in the first portion of the liquid composition are cured (polymerized) to form a primed tooth surface.

In accordance with a preferred embodiment of the invention is provided a method of adhering a restorative material to a dental tooth by applying a liquid composition to at least a portion of the tooth to form a treated surface. The composition includes at least 50 percent by weight of a volatile solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which is adapted to adhere to dentin with a bond strength of at least 12 MPa. Restorative material is then affixed to at least a portion of the treated surface with a bond strength of at least about 12 MPa.

Acid-etching of enamel may be done but is not necessary. To fill deep tooth cavities it is preferred to cover the dentine closest to the pulp of the tooth with a hard-setting calcium hydroxide liner (such as DYCAL, sold by Dentsply International Inc.) leaving the rest of the cavity floor and walls free for chemical bonding with a dental restorative such as Dyract, sold by Dentsply International Inc.

Preferred volatile solvents include, ethanol, methanol, isopropanol, dimethyl ketone, ethylmethyl ketone, and mixture of these.

Preferred monomers for use in primer adhesive compositions in accordance with the invention have a solubility in water of less than about 5%, and more preferably have a solubility in water of less than 1%. Exemplary monomers include triethylene glycol dimethacrylate, tetraethyleneglycol dimethacrylate, glycerol-1,2-dimethacrylate, glycerol-1,3-dimethacrylate, the reaction product of butanediol diglycidyl ester and methacrylic acid, tetrahydrofurfural methacrylate, methacryloxyethyl maleic ester, methacryloxyethyl succinate, urethane dimethacrylate, Bis-GMA, Ethoxylated bisphenol-A dimethacrylate, bisphenol-A dimethacrylate, and mixtures thereof. Monomers having a solubility in water higher than 5% are less preferred. Monomer having a solubility in water less than about 1% are more preferred. Highly water soluble monomers such as hydroxyethyl methacrylate and hydroxypropyl methacrylate tend to provide lower adhesion and are less suitable for use in compositions of the invention.

As the free radical-polymerizable monomer or prepolymer to be employed in this invention, use may be made of any monomer, dimer, trimer, or other oligomer of the type that is usable in dental applications. Thus, the polymerizable monomer portion of the present adhesive composition generally comprises one or more monofunctional or polyfunctional ethylenically unsaturated monomers or prepolymers, e.g., dimers, trimers, and other oligomers, or mixtures or copolymers thereof, based on acrylic or methacrylic or itaconic acid, or derivatives thereof, including their esters which can be polymerized by free radical initiation. These materials include, but are not limited to acrylic and methacrylic acid, itaconic acid and the like, acrylic or methacrylic or itaconic acid esters of monohydric or polyhydric alkanols or polyhydric alcohols containing at least one phenyl group. Examples of such compound include monovinylmethacrylates, e.g., methylmethacrylate, ethyl acrylate, propyl methacrylate, hydroxyethylmethyacrylate, hydroxypropylmethacrylate, diethylene glycol acrylate, triethylene glycol acrylate, the monoester of trimellitic acid with hydroxyethyl methacrylate, hydroxypropyl itaconate and the like, esters of aliphatic polyhydric alcohols, such as for example, the di- and polyacrylates, the di- and polymethacrylates, and the di- and polyitaconates of alkylene glycols, alkoxylene glycols, alicyclic glycols and higher polyols, such as ethylene glycol, triethylene glycol, tetraethylene glycol, tetramethylene glycol, trimethylolethane, trimethylolpropane, pentaerythritol, dipentaerythritol, tripentaerythritol, and the like, or mixtures of these with each other or with their partially esterified analogs, and their prepolymers, such compound or mixture optionally having free hydroxyl content. Typical compounds of this type, include but are not limited to, trimethylolpropane triacrylate, trimethylolethane triacrylate, trimethylolpropane trimethacrylate, trimethylolethane trimethacrylate, tetram-ethylene glycol dimethacrylate, ethylene glycol dimethacrylate, triethylene glycol dimethacrylate, tetraethylene glycol diacrylate, tetraethylene glycol dimethacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexacrylate, tripentaerythritol octaacrylate, pentaerythritol dimethacrylate, pentaerythritol trimethacrylate, dipentaerythritol dimethacrylate, glycerin trimethacrylate, ethylene glycol dimethacrylate, butanediol dimethacrylate, trimethylolpropane trimethacrylate, tetramethylolmethane tetramethacrylate, bisphenol-A dimethacrylate, bisphenol-A diglycidyl methacrylate, 2,2,'-bis-(4-methacryloxyethoxyphenyl) propane and so on.

Also included among the polymerizable monomers which may be used are the vinyl urethane or urethane-acrylate prepolymers which are well known in the art. These prepolymers are polymerizable by free radical initiation and may be prepared, for example, by reacting an organic diisocyanate or an isocyanate-terminated urethane prepolymer with an ethylenically unsaturated monomer which is reactive with the diisocyanate or urethane prepolymer. These polymers also may be prepared by reacting a hydroxyl-containing material, such as a polyol or a hydroxyl-terminated urethane prepolymer with an ethylenically unsaturated monomer which is reactive with the polyol or hydroxyl-terminated urethane. The urethane prepolymers, which may be linear or branched, carry isocyanate end groups and generally are prepared by reacting a compound having hydroxyl functionality with a molar excess of diisocyanate.

Any of a wide variety of diisocyanates may be used to prepare the isocyanate-terminated urethane prepolymer including aliphatic, cycloaliphatic, heterocyclic, and aromatic diisocyanates, and combinations of these. Examples include, but are not limited to, 2,4-tolylene diisocyanate, 2,6-tolylene diisocyanate, 1,4-phenylene diisocyanate, 2,2,4-trimethyl hexamethylene diisocyanate, hexamethylene diisocyanate, 1,4-naphthalene diisocyanate, 1,5-naphthalene diisocyanate, 4,4,'-diphenylmethane diisocyanate, p,p,'-diphenyl diisocyanate, butylene-1,4-diisocyanate, ethylene diisocyanate, trimethylene diisocyanate, tetramethylene-1,4-diisocyanate, butylene-2,3-diisocyanate, cyclohexylene-1,2-diisocyanate, methylene-bis-(4-phenyl-isocyanate), diphenyl-3,3,'-dimethyl-4,4,'-diisocyanate, xylylene diisocyanate, cyclohexane-1,4-diisocyanate, 1-methoxyphenyl-2,4-diisocyanate and the like, and mixtures thereof.

A wide variety of compounds having hydroxyl functionality may be used to form the isocyanate-terminated urethane prepolymers. For example, diols of the structure

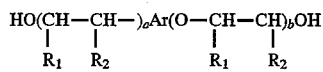

may be used, where R1 and R2 are hydrogen atoms or alkyl groups, e.g., methyl, and Ar is a divalent aromatic group in which each free valency is on an aromatic carbon atom, and where a and b, independently, may be zero or an integer. Other suitable hydroxyl containing compounds include diols and polyols such as ethylene glycol, propylene glycol, triethylene glycol, tetramethylene glycol, trimethylolpropane, pentaerythritol, dipentaerythritol, and the like, or esters of acrylic acid, methacrylic acid or itaconic acid or the like with aliphatic polyhydric alcohols. Among the more preferred hydroxyl containing compounds are the esters of acrylic or methacrylic acid and a hydroxyalkanol of at least two carbon atoms such as hydroxyethyl acrylate, hydroxyethyl methacrylate, hydroxypropyl acrylate, hydroxypropyl methacrylate, hydroxyisopropyl methacrylate, and the like.

Formation of the isocyanate terminated urethane prepolymers may be assisted by the use of a catalyst known in the art to assist polyurethane formation, for example, tertiary amines and metal salts, e.g., tin salts, titanium salts and the like.

To form the vinyl urethane or urethane-acrylate prepolymer starting materials, an isocyanate-terminated urethane prepolymer or a diisocyanate is reacted with an ethylenically unsaturated compound having hydroxyl functionality. These compounds include for example, esters of acrylic acid, methacrylic acid or itaconic acid with aliphatic polyhydric alcohols, such as hydroxyethyl acrylate, hydroxypropyl methacrylate or the like. The resulting vinyl urethanes are well known in the art and are described for example, in U.S. Pat. No. 3,629,187 to Waller, U.S. Pat. No. 3,759,809 to Carlick et al, U.S. Pat. No. 3,709,866 to Waller and U.S. Pat. No. 4,459,193 to Ratcliffe et al, and all of these patents are incorporated herein by reference.

Formation of the vinyl urethane prepolymers may be assisted by the use of the same catalysts noted above, namely, tertiary amines and metal salts.

The foregoing list of polymerizable ethylenically unsaturated monomers and prepolymers is intended to be exemplary only, and other known polymerizable materials can be used in compositions of this invention.

In accordance with a preferred embodiment of the invention two or more ethylenically unsaturated compounds are included in dental treatment compositions. In a preferred embodiment of the invention the polymerizable monomer is liquid at temperatures from about 20° C. to about 25° C.

Preferred monomers are TEGDMA, glyceryl dimethacrylate, polyethylene glycol dimethacrylate, trimethylolpropane, trimethacrylate, urethane dimethacrylate (UDMA), EBPDMA, and ethylene glycol dimethacrylate.

Preferred solvents are ethanol, 2-propanol, and dimethyl ketone.

A preferred bonding composition in accordance with a preferred embodiment of the invention includes 10 percent by weight of ENTA; 10 percent by weight of urethane diacrylate; 2.5 percent by weight of TEGDMA; 0.01 to about 1 percent by weight of glutaraldehyde; 0.2 percent by weight of CQ; 0.4 percent by weight of EDAB; 0.1 percent by weight of BHT; from 80.8 to about 81.8 percent by weight of dimethyl ketone.

A preferred etchant includes 10 percent by weight of $H_3PO_4$; 2.5 percent by weight of $AlCl_3$; 87.5 percent by weight of water.

Exemplary acrylic monomers for use in compositions of the invention include: 1,4-butanediol dimethacrylate (BDEM); glyceryl dimethacrylate (GlyDM); hydroxyethyl methacrylate (HEMA); triethyleneglycol dimethacrylate (TGD); tetrahydrofuran dimethacrylate (THFMA). Having generally described the invention, a more complete understanding can be obtained with reference to certain specific examples, which are included for purposes of illustration only. It should be understood that the invention is not limited to the specific details of the Examples.

EXAMPLE 1

A) Priming Adhesive Composition

A priming and adhesive polymerizable composition in accordance with the invention is formed by stirring 10.00 grams of 7,7,9,63,65 hexamethyl-4,13,60,69-tetra-oxo-3,14, 19,24,29,34,39,44,49,54,59,70-dodecanaoxa-5,12,61,68-tetra-azadoheptacontane-1,72 diyl-dimethacrylate, (also known as urethane dimethacrylate resin); 5.00 grams of 2,2,6–6 tetra acryloxyloxymethyl-4, 8 dioxa-9-oxo-11-undecyl phosphoric acid, also known as dipentaerythritol pentacrylate phosphoric acid ester (PENTA); 5.00 grams of 2-propenoic acid, 1-methyl-1, 2-ethanediyl-bis (oxy-21-ethanediyl)ester; also known as triethylene glycol dimethacrylate (TEGMA); 0.01 grams of phenol, 2,6-bis-(1,1-dimethethyl-4-methyl), also known as butylated hydroxytoluene (BHT); 0.020 grams of bicyclo [2.2.1] heptane-2, 3-dione 1,7,7-trimethyl, also known as camphorquinone; 0.60 grams of 4-Ethyl dimethyl aminobenzoate (DMABE), and 79.19 grams of dimethyl ketone also known as dimethyl ketone.

B) Priming a Tooth Surface

A dental tooth surface of dentine and enamel is sanded using 320 grit silicon carbide paper, then sanded using 600 grit silicon carbide paper. Then the sanded tooth surface is blotted dry with an absorbent material. Three drops of the priming adhesive composition, made by following the procedure of Example 1 Section A, are removed from a bottle and applied directly onto a brush. The priming adhesive composition is applied to the sanded tooth surface with the brush to thoroughly wet the sanded dentine and enamel surface. The priming adhesive coating surface is left undisturbed for 30 seconds. Excess solvent is then removed by blowing air from an air tank over the coated tooth surface. The priming adhesive composition is then cured for 20 seconds using a Max lite light curing device having an 8 mm long probe to form a cured priming adhesive treated tooth.

C) Applying Restorative

Immediately APH restorative, sold by Dentsply International Inc. is applied to the cured priming adhesive. The restorative is cured by irradiating for 40 seconds with light from a Max lite light curing device. The restorative bonds to the treated tooth surface with a bond strength of 7.7 MPa.

The procedure of Example 1 is repeated fifty (50) times and provides a retention rate at one year of about 98 percent.

EXAMPLE 2

A) Priming a Tooth Surface

A dental tooth surface of dentine and enamel is sanded using 320 grit silicon carbide paper, then sanded using 600 grit silicon carbide paper. Then the sanded tooth surface is blotted dry with an absorbent material. Three drops of the priming adhesive composition, made by following the procedure of Example 1 Section A, are removed from a bottle and applied directly onto a brush. The priming adhesive composition is applied to the sanded tooth surface with the brush to thoroughly wet the sanded dentine and enamel surface. The priming adhesive coating surface is left undisturbed for 15 seconds.

B) Treating the Primed Tooth Surface

A second layer of the priming adhesive composition, is then applied to the cured primed tooth by brush. Excess solvent of the second layer is removed after 15 seconds by blowing with air from an air tank. The priming adhesive composition is then cured for 20 seconds using a Max lite light curing device having an 8 mm long probe to form a cured priming adhesive coated portion of a tooth.

C) APH restorative, sold by Dentsply international Inc. is applied to the cured priming adhesive coated portion of the tooth. The restorative is then cured by irradiating for 40 seconds with light from a Max lite light curing device which bonds the restorative to the treated tooth surface with a bond strength of 16.7 MPa.

EXAMPLE 3

A) Priming a Tooth Surface

A dental tooth surface of dentine and enamel is sanded using 320 grit silicon carbide paper, then sanded using 600 grit silicon carbide paper. Then the sanded tooth surface is blotted dry with an absorbent material. Three drops of the priming adhesive composition, made by following the procedure of Example 1 Section A, are removed from a bottle and applied directly onto a brush. The priming adhesive composition is applied to the sanded tooth surface with the brush to thoroughly wet the sanded dentine and enamel surface. The priming adhesive coating surface is left undisturbed for 15 seconds. The priming adhesive composition is then cured for 20 seconds using a Max lite light curing device having an 8 mm long probe to form a cured priming adhesive coated portion of a tooth.

B) Treating the Primed Tooth Surface

A second layer of the priming adhesive composition, is applied to the cured primed tooth by brush. Excess solvent of the second layer is removed after 15 seconds by blowing with air from an air tank. The priming adhesive composition is then cured for 20 seconds using a Max lite light curing device having an 8 mm long probe to form a cured priming adhesive coated portion of a tooth.

C) APH restorative, sold by Dentsply International Inc. is applied to the cured priming adhesive coated portion of the tooth. The restorative is then cured by irradiating for 40 seconds with light from a Max lite light curing device which bonds the restorative to the treated tooth surface.

In the Examples and throughout this disclosure unless otherwise indicated shear bond strength is determined by treating extracted human teeth in 1% sodium hypochlorite for 18 to 24 hours, washing with water, and storing in distilled water in a refrigerator at about 4° C. until needed. The teeth are mechanically wet sanded with 120/320/600 grit carborundum paper until the dentin is exposed. Each tooth sample is then prepared by blotting dry exposed dentin with absorbent material, such as Kimwipe; etching dentin with 10% phosphoric acid for 15 seconds; rinsing with water for 15 seconds; and then blotting dry with absorbent material, such as Kimwipe. Two coats of adhesive composition are then applied to dentin with a brush for 30 seconds; dried with oil-free air for five seconds; curing for 20 seconds with a Max™Lite light curing unit. Prisma®APH™ restorative is placed in a cylindrical plastic matrix with a 3.68 mm inside diameter, set on the treated dentin and cured for 40 seconds. The specimens are stored in distilled water for approximately 24 hours at 37° C. Each specimen is mounted vertically in a plastic cylinder with self cure polymethyl methacrylate so that the dentin surface is parallel to the Instron needle; and then debonded on an Universal Instron with a crosshead speed of 5 mm/minute. The bond strength is then calculated in MPa.

While present embodiments of the invention and methods of practicing the same have been illustrated and described, it will be recognized by those skilled in the art that this invention may be otherwise variously embodied and practiced within the scope of the following claims.

What is claimed is:

1. A method for adhesion of restorative material to a natural tooth, comprising:

a) applying a first portion of photopolymerizable liquid primer/adhesive dental composition to tooth surface, said composition consisting essentially of a photoinitiator, at least fifteen percent by weight polymerizable material and at least fifty percent by weight of a volatile organic solvent, said polymerizable material comprising one or more polymerizable acrylate compounds at least a portion of said polymerizable acrylate compounds being a multifunctional polymerizable compound having at least three acrylate moieties and one phosphate moiety, b) impinging light on said first portion of said liquid composition whereby a portion of said first portion of said liquid composition polymerizes to form a first coating on said tooth, c) applying a second portion of said liquid composition to said first coating, and d) impinging light on said second portion of said liquid composition whereby at least a portion of said second portion of said composition polymerizes to form a treated tooth surface adapted to retain a restorative material with an adhesion to natural tooth material of at least 12 MPa.

2. The method of claim 1 wherein said tooth comprises dentin and a dentin layer and at least part of said first portion of said liquid composition substantially penetrates said dentin layer to contact said dentin.

3. The method of claim 1 wherein said first and second portions of said liquid composition polymerize to form a substantially uniform adhesive interface having a thickness of at least 10 microns.

4. The method of claim 1 further comprising applying a restorative composition to said treated tooth surface, and photocuring said restorative composition to form a restorative filling having a clinical retention rate after one year of at least 98 percent.

5. The method of claim 1 further comprising applying a photopolymerizable dental restorative composition to said treated tooth surface, impinging light on said restorative composition whereby at least a portion of said restorative composition polymerizes to form a cured restorative material adhered with a first bond strength to said treated tooth surface.

6. The method of claim 5 wherein said first bond strength is greater than a bond strength of a bond formed between said restorative material and a tooth formed by a) applying a first portion of photopolymerizable liquid primer/adhesive dental composition to tooth surface, c) applying a second portion of said liquid composition to said first coating, and substantially immediately conveying air to said second portion of said liquid composition, d) impinging light on said first and second portions of said liquid composition.

7. The method of claim 1 wherein said liquid composition is adapted to form a polymeric material which adheres to dentin with a bond strength of at least 15 MPa.

8. The method of claim 7 further comprising effectively removing a layer from said tooth surface, before said applying said first portion of liquid composition.

9. The method of claim 7 wherein said tooth comprises a layer and at least a portion of said layer is effectively removed at neutral pH.

10. The method of claim 7 wherein said composition comprises at least 7 percent by weight of said multifunctional polymerizable compounds.

11. The method of claim 7 wherein said solvent is dimethyl ketone or methyl ethyl ketone and said bond strength is at least 15 MPa.

12. The method of claim 7 wherein said composition comprises at least 75 percent by weight of said solvent.

13. The method of claim 7 wherein at least a portion of said multifunctional polymerizable compounds are phosphate esters.

14. The method of claim 7 wherein at least a portion of said multifunctional compounds have a chemical structure within the scope of the general formula: $(R)_n$—Z—$(A)_m$ wherein each R independently is an acrylate containing moiety, Z is an organic moiety, each A independently is an acid or acid ester, n is an integer greater than 2, m is an integer of 1 or more.

15. The method of claim 7 wherein said solvent is dimethyl ketone and said bond strength is at least 15 MPa.

16. The method of claim 15 wherein at least a portion of said polymerizable compounds are acids and said acids comprise at least 2 percent by weight of said composition.

17. The method of claim 15 wherein said composition further comprises a polymerizable compound having at least two acrylate moieties and a gram molecular weight greater than 200, said polymerizable compound being adapted to form an elastomer when polymerized.

18. The method of claim 15 wherein said liquid composition further comprises carboxylic acids.

19. The method of claim 15 further comprising conveying air to said first and second portions of said liquid on said layer.

20. The method of claim 15 further comprising conveying air against said second portion of said liquid composition.

21. The method of claim 20 wherein said liquid dental composition comprises at least 70% of a volatile solvent.

22. The method of claim 20 wherein said first portion of said liquid composition is left on said surface undisturbed for at least 15 seconds.

23. The method of claim 21 wherein said solvent is miscible with water and when mixed with water brings about a substantial degree of increased vaporization of the water in-situ at said treated surface.

24. The method of claim 7 wherein said liquid dental composition has a viscosity of less than 400 centipoise.

25. The method of claim 7 wherein said liquid dental composition comprises oligomer having a weight average molecular weight greater than 600.

26. The method of claim 20 wherein before said applying said first of said liquid composition at least a portion of said tooth is treated by steps comprising:

(1) applying a dilute acid to said tooth surface to form an etched tooth surface, (2) rinsing said dilute acid from said etched tooth surface to form a rinsed etched surface, and (3) partially drying said rinsed etched surface to form a wetted etched surface.

27. The method of claim 26 wherein said first portion of said liquid composition remains undisturbed on said surface for at least 20 seconds, has a viscosity of less than 300 centipoise and comprises at least 70% of a water miscible volatile solvent, and wherein said liquid composition further comprises at least 2% of an oligomer having a weight average molecular weight greater than 650.

28. A method of adhering a restorative material to a natural tooth, comprising:

a) applying a first portion of photopolymerizable liquid primer/adhesive dental composition to tooth surface, said composition consisting essentially of a photoinitiator, at least fifteen percent by weight polymerizable material and at least fifty percent by weight of a volatile organic solvent, said polymerizable material comprising polymerizable acrylate compounds, at least a portion of said polymerizable acrylate compounds being a dimethacrylate compound and at least a portion of said polymerizable acrylate compounds being a multifunctional polymerizable compound having at least three acrylate moieties and one phosphate moiety, b) impinging light on said first portion of said liquid composition whereby a portion of said first portion of said liquid composition polymerizes to form a first coating on said tooth, c) applying a second portion of said liquid composition to said first coating, and d) impinging light on said second portion of said liquid composition whereby at least a portion of said second portion of said composition polymerizes to form a treated tooth surface adapted to retain a restorative material to natural tooth material with an adhesion of at least 12 MPa.

29. The method of claim 28 wherein said liquid composition remains on said surface substantial undisturbed for at least 20 seconds and has a viscosity of less than 300 centipoise and comprises at least 70% of a water miscible volatile solvent, and at least 2% of an oligomer having a weight average molecular weight greater than 650.

30. A method of treating a natural tooth, comprising:

a) applying a first portion of photopolymerizable liquid primer/adhesive dental composition to tooth surface to form a first coating, said composition comprising a photoinitiator, at least fifteen percent by weight polymerizable material and at least seventy percent by weight of acetone said polymerizable material comprising one or more polymerizable acrylate compounds at least a portion of said polymerizable acrylate compounds being a multifunctional polymerizable compound having at least three acrylate moieties and one phosphate moiety, b) applying a second portion of said liquid composition to said first coating, and conveying air to said second portion of said liquid composition, and c) impinging light on said second portion of said liquid composition whereby at least a portion of said second portion of said composition polymerizes to form a treated tooth surface adapted to retain a restorative material to natural tooth material with an adhesion of at least 12 MPa.

31. The method of claim 30 further comprising applying a restorative composition to said treated tooth surface, and photocuring said restorative composition to form a restorative filling having a clinical retention rate after one year of at least 98 percent.

32. The method of claim 30 further comprising applying a photopolymerizable dental restorative composition to said treated tooth surface, impinging light on said restorative composition whereby at least a portion of said restorative composition polymerizes to form a cured restorative material adhered with a first bond strength to said treated tooth surface.

33. The method of claim 32 wherein said first bond strength is greater than a comparative bond strength of a bond between said restorative material and a tooth formed essentially by a) applying a first portion of said liquid composition to said treated tooth surface, b) impinging light on said first portion of said liquid composition, c) applying a photopolymerizable dental restorative composition to said treated tooth surface, d) impinging light on said restorative composition whereby at least a portion of said restorative composition polymerizes to form a cured restorative material adhered with a comparative bond strength to said treated tooth surface.

34. A method for adhesion of restorative material to a natural tooth, comprising:

a) applying a first portion of photopolymerizable liquid primer/adhesive dental composition to an etched tooth surface, said composition comprising a photoinitiator at least fifteen percent by weight polymerizable material and at least fifty percent by weight of a volatile organic solvent, said polymerizable material comprising one or more polymerizable acrylate compounds at least a portion of said polymerizable acrylate compounds being a multifunctional polymerizable compound having at least three acrylate moieties and one phosphate moiety, b) impinging light on said first portion of said liquid composition whereby a portion of said first portion of said liquid composition polymerizes to form a first coating on said tooth, c) applying a second portion of said liquid composition to said first coating, d) impinging light on said second portion of said liquid composition whereby at least a portion of said second portion of said composition polymerizes to form a treated tooth surface adapted to retain a restorative material to natural tooth material with an adhesion of at least 12 MPa.

35. The method of claim 1 further comprising leaving said first portion of said liquid composition undisturbed for at least 15 seconds on the surface and then conveying air against said first portion of the liquid on the surface.

36. The method of claim 35 further comprising conveying air to said second portion of said liquid composition substantially immediately after said applying of said second portion of said liquid composition to said first coating.

37. The method of claim 1 wherein said restorative material is retained to said treated tooth surface with a clinical retention rate of at least 95 percent with acceptable marginal integrity.

38. A method for clinical retention of restorative material by a natural tooth with acceptable marginal integrity, comprising:

a) applying a first portion of photopolymerizable liquid primer/adhesive dental composition to tooth surface, said composition comprising a photoinitiator, at least fifteen percent by weight polymerizable material and at least seventy percent by weight of a volatile organic solvent, said polymerizable material comprising one or more polymerizable acrylate compounds at least a portion of said polymerizable acrylate compounds being a multifunctional polymerizable compound having at least three acrylate moieties and one phosphate moiety, b) after leaving the first portion of said liquid composition on the tooth surface undisturbed for at least 15 seconds on the surface, conveying air against the first portion of the liquid on said surface, impinging light on said first portion of said liquid composition whereby a portion of said first portion of said liquid composition polymerizes to form a first coating on said tooth, c) applying a second portion of said liquid composition to said first coating, and substantially immediately conveying air to said second portion of said liquid composition, d) impinging light on said first and second portions of said liquid composition whereby at least a portion of said second portion of said composition polymerizes to form a treated tooth surface adapted to retain a restorative material with an adhesion to natural tooth material of at least 12 MPa at a clinical retention rate of at least 95 percent with acceptable marginal integrity.

39. The method of claim 38 wherein said liquid composition is adapted to form a polymeric material which adheres to dentin with a bond strength of at least 15 MPa.

40. A method of adhering a restorative material to a natural tooth, comprising:

a) applying a first portion of photopolymerizable liquid primer/adhesive dental composition to tooth surface, said composition comprising a photoinitiator, at least fifteen percent by weight polymerizable material and at least seventy percent by weight of a volatile organic solvent, said polymerizable material comprising one or more polymerizable acrylate compounds at least a portion of said polymerizable acrylate compounds being a multifunctional polymerizable compound having at least three acrylate moieties and one phosphate moiety, b) after leaving said first portion of said liquid composition on said tooth surface undisturbed for at least 15 seconds on said surface, conveying air against said first portion of said liquid on said surface, impinging light on said first portion of said liquid composition whereby a portion of said first portion of said liquid composition polymerizes to form a first coating on said tooth, c) applying a second portion of said liquid composition to said first coating, and substantially immediately conveying air to said second portion of said liquid composition, and d) impinging light on said first and second portions of said liquid composition whereby at least a portion of said second portion of said composition polymerizes to form a treated tooth surface adapted to retain a restorative material to natural tooth material with an adhesion of at least 12 MPa at a clinical retention rate of at least 98 percent with acceptable marginal integrity.

41. The method of claim 40 wherein said liquid composition is adapted to form a polymeric material which adheres to dentin with a bond strength of at least 15 MPa.

42. A method for clinical retention of restorative material by a natural tooth with acceptable marginal integrity, comprising:

a) applying a first portion of photopolymerizable liquid primer/adhesive dental composition to an etched tooth surface, said composition comprising a photoinitiator, at least fifteen percent by weight polymerizable material and at least fifty percent by weight of a volatile organic solvent, said polymerizable material comprising one or more polymerizable acrylate compounds at least a portion of said polymerizable acrylate compounds being a multifunctional polymerizable compound having at least three acrylate moieties and one phosphate moiety, b) after leaving said first portion of said liquid composition on said tooth surface undisturbed for at least 15 seconds on said surface, conveying air against said first portion of said liquid on said surface, impinging light on said first portion of said liquid composition whereby a portion of said first portion of said liquid composition polymerizes to form a first coating on said tooth, c) applying a second portion of said liquid composition to said first coating, and substantially immediately conveying air to said second portion of said liquid composition, d) impinging light on said first and second portions of said liquid composition whereby at least a portion of said second portion of said composition polymerizes to form a treated tooth surface adapted to retain a restorative material to natural tooth material with an adhesion of at least 12 MPa at a clinical retention rate of at least 95 percent with acceptable marginal integrity.

43. The method of claim 42 wherein said liquid composition is adapted to form a polymeric material which adheres to dentin with a bond strength of at least 15 MPa.

* * * * *